United States Patent [19]
Merkel

[11] Patent Number: 5,182,938
[45] Date of Patent: Feb. 2, 1993

[54] METHOD AND APPARATUS FOR DETECTING BUBBLES IN PRESSURIZED LIQUID DISPENSING SYSTEMS

[75] Inventor: Stephen L. Merkel, Bay Village, Ohio

[73] Assignee: Nordson Corporation, Westlake, Ohio

[21] Appl. No.: 659,842

[22] Filed: Feb. 22, 1991

[51] Int. Cl.⁵ .............................................. G01N 7/00
[52] U.S. Cl. .................................. 73/19.05; 73/61.78
[58] Field of Search ................ 73/61 R, 19.05, 61.78, 73/61.47, 61.41; 222/55

[56] References Cited

U.S. PATENT DOCUMENTS

| | | | |
|---|---|---|---|
| 3,237,634 | 3/1966 | Colby | 137/82 |
| 3,790,042 | 2/1974 | McCormick et al. | 222/52 |
| 3,830,095 | 8/1974 | Jaross | 73/19 |
| 3,863,244 | 1/1975 | Lichtblau | 340/280 |
| 3,898,637 | 8/1975 | Wolstenholme | 340/239 R |
| 3,958,092 | 5/1976 | Hoover | 200/81.9 M |
| 4,014,206 | 3/1977 | Taylor | 73/19 |
| 4,072,934 | 2/1978 | Hiller | 340/243 |
| 4,166,936 | 9/1979 | Tice | 200/82 E |
| 4,215,746 | 8/1980 | Hallden et al. | 166/53 |
| 4,255,088 | 3/1981 | Newton et al. | 73/19.05 X |
| 4,430,886 | 2/1984 | Rood | 73/37 |
| 4,613,059 | 9/1986 | Merkel | 222/52 |
| 4,662,540 | 5/1987 | Schroter | 222/55 |
| 4,779,762 | 10/1988 | Klein et al. | 222/52 |
| 4,842,162 | 3/1988 | Merkel | 222/1 |
| 4,922,852 | 5/1990 | Price | 118/683 |
| 5,086,640 | 2/1992 | Nagata et al. | 73/661 |

FOREIGN PATENT DOCUMENTS 0163069 12/1985 European Pat. Off. .
8607540 9/1987 Fed. Rep. of Germany .

OTHER PUBLICATIONS

Sense-A-Bead; Robotics, Inc.

Primary Examiner—Hezron E. Williams
Assistant Examiner—Joseph W. Roskos
Attorney, Agent, or Firm—Raymond J. Slattery, III

[57] ABSTRACT

A pressure transducer (58) generates an instantaneous pressure of a pressurized liquid, such as an adhesive, sealant, or caulk, being dispensed from a dispenser (52). The signal is received by a filter for filtering out non-bubble pressure disturbances. The filter includes comparators (106, 108); detection circuitry (112, 120) and timers (116, 124) or counters. An alarm indicating the passing of a bubble is indicated in response to signals which pass both the filters.

19 Claims, 4 Drawing Sheets

METHOD AND APPARATUS FOR DETECTING BUBBLES IN PRESSURIZED LIQUID DISPENSING SYSTEMS

BACKGROUND OF THE INVENTION

This invention relates generally to the dispensing of fluid materials onto substrates. More particularly, the invention relates to the detection of bubbles in pressurized liquid dispensing systems. Specifically, this invention relates to the detection of the presence of air bubbles in a fluid stream delivered from a nozzle of a system for dispensing adhesives, sealants, or caulks to a substrate.

The presence of an air bubble passing through a nozzle of a dispensing system may cause a void to occur in the stream of the material being dispensed, and, in turn, the bead deposited upon the substrate. If the occurrence of the air bubble is small, the effect on the resulting bead may be minimal. However, if the air bubble is large, the effect may be to produce a discontinuancy in the bead. In some applications, discontinuities of the bead may not be critical, however, in others they may be. For example, discontinuities in a bead of the adhesive/sealant applied to a windshield may not only affect its ability to act on a moisture barrier, but it also may affect the strength of the bond of the windshield to the vehicle.

Schroter U.S. Pat. No. 4,662,540 illustrates one attempt to detect the presence of air bubbles in sealants, mastics, and adhesives. In this system, a pressure transducer produces an electrical signal which corresponds to the instantaneous pressure of the fluid. This electrical signal is then differentially amplified and compared to a threshold level. In other words, U.S. Pat. No. 4,662,540 teaches the comparison of the rate of change of the pressure waveform to that of a preset reference. The rate of change of the waveform produced by the pressure sensor in excess of the threshold level is used to distinguish between bubbles and other disturbances in the pressure of the fluid which is presumed to have lower rates of changes than bubbles. However, this method is believed to have the disadvantage of not being able to distinguish between bubbles and other waveforms which may have a rate of change which resembles bubbles, but which are in fact other disturbances.

When an air bubble passes through a nozzle, a pressure disturbance occurs in the fluid upstream (in the opposite direction of the flow of the fluid) of the nozzle. The amplitude of this pressure disturbance or waveform may be large or it may be small, but its profile is distinctive. The profile begins with a transition of a negative-going extrusion of pressure, followed by a recovery portion which then overshoots the normal pressure level to produce a positive-going extrusion of pressure, before recovering to the normal operating pressure. This waveform resembles that of a pulse that is sent down a rope or a whip when it is cracked. However, other waveforms that are not bubbles may also have similar types of profiles.

Similar types of waveforms, for example, may be produced by gun turn-on and turn-off transients, pressure fluctuations of the dispensing system, electrical interference, or the passing of a solid or semi-solid chunk or piece of material (such as cured fluid) through the dispensing system. Therefore, a detector which only distinguishes disturbances based on the rate of change of the pressure waveform may result in false positive indications of bubbles.

U.S. Pat. No. 4,662,540 attempts to solve the gun turn-on and turn-off transients by disabling the system while the gun is being turned on or turned off. This, however, means the bubble detection system is blind during certain portions of the operation. It also does not distinguish between the other transient disturbances, such as the passing of a solid or semi-solid chunk or piece of material and those of bubbles.

SUMMARY OF THE INVENTION

It is, therefore, an object, according to one embodiment of the invention, to provide a method and a means for distinguishing between bubbles and other pressure disturbances.

A feature, according to one embodiment of the invention, is a filtering means for filtering out pressure transients which are not bubble related.

It is a feature, according to one embodiment of this invention, to produce a signal relating to the fluid pressure and to compare the time intervals between reference crossings of the signal to a respective reference.

It is an advantage of this invention that the bubble detecting system can be continuously operated, eliminating the need to selectively enable/disable the system in order to eliminate false indications of bubbles. As a result, the bubble detection system is not blind during portions of the dispensing of the fluid.

These and other objects, features, and advantages can be accomplished by a bubble detector comprising: a means for detecting pressure transients of the pressurized liquid; a means for filtering out pressure transients having amplitudes less than predetermined reference levels; a bandpass filter means for filtering out pressure transients having a period of less than a first predetermined value and also those having a period greater than a second predetermined value, wherein non-bubble related transients are filtered out, and generating a signal in response thereto; and a bubble indication means, responsive to the signals received from the bandpass filter means for indicating the occurrence of a bubble.

The above may also be accomplished by: a) dispensing the pressurized liquid from a nozzle means of a dispensing means; b) sensing the pressure of the pressurized liquid passing through the nozzle means; c) generating a signal in response to the pressure sensed; d) filtering the signals by filtering out signals below a predetermined reference level, rapidly changing short duration signals, and slow changing, long duration signals; and e) indicating the occurrence of a bubble in response to the filtered signal.

The above may also be further accomplished in one particular embodiment by an apparatus for dispensing pressurized fluid material comprising: inlet means for receiving the fluid connectable to a source of fluid; nozzle means downstream of the inlet means for discharging the fluid; a sensor means operably connected to the nozzle means for generating a pressure signal in response to changes in the pressure of the fluid; an amplifier means for amplifying the generated pressure signal; a first and second comparator, each receiving the amplified signal and comparing the amplified signal to a first and second reference level respectively; and means responsive to signals from the first and second comparators for producing a signal indicating the presence of a bubble and wherein the means includes a timing means and latching means.

BRIEF DESCRIPTION OF THE DRAWINGS

The following is a brief description of the drawings in which like parts may bear like reference numerals and in which.

DETAILED DESCRIPTION OF THE INVENTION

Figure 1:
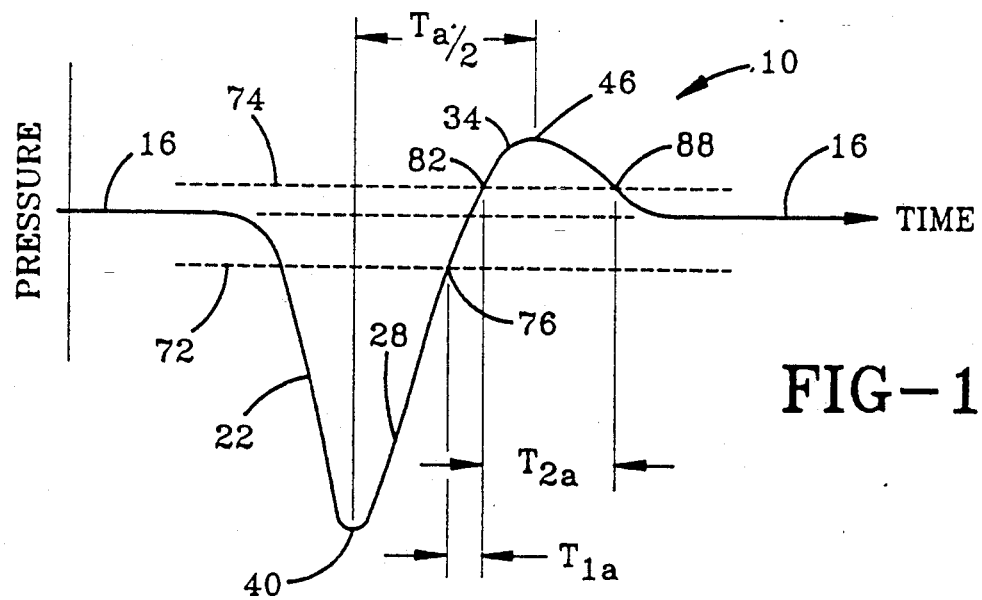
FIGS. 1 through 3 are characteristic curves showing pressure versus time characteristics of a bubble, a chunk, and a pressure transient in a pressurized fluid dispensing apparatus, respectively.
Figure 2:
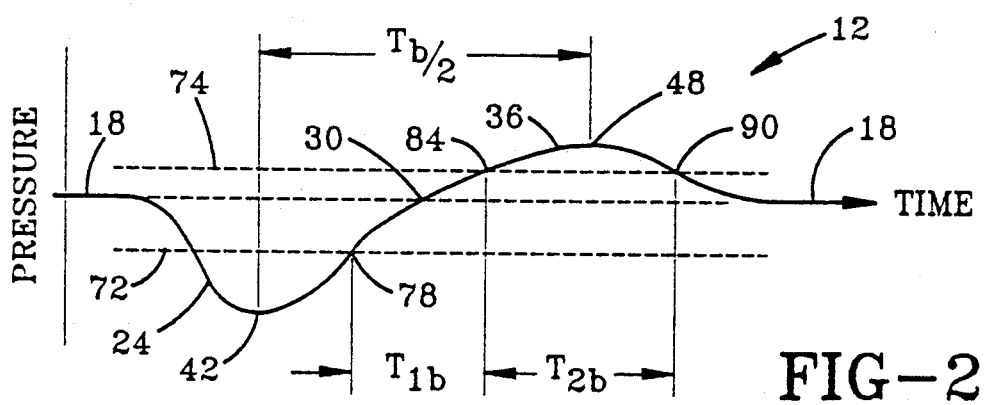
Figure 3:
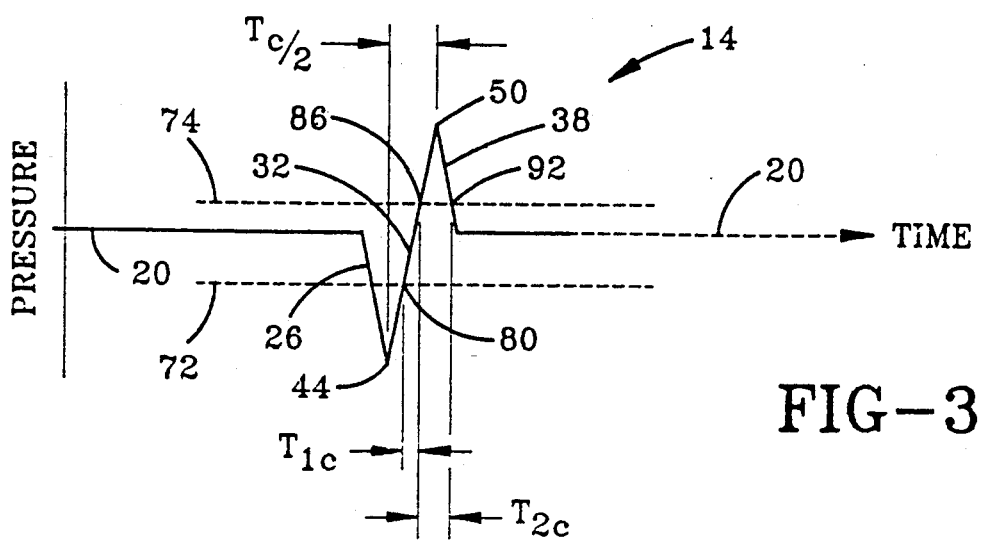

With reference to FIGS. 1, 2, and 3, there is illustrated pressure waveforms of a bubble, a chunk, and a transient produced by the on/off cycle of the dispenser, shown generally as reference numerals 10, 12, 14, respectively. In each case, prior to a pressure disturbance, the pressure of the fluid is at the normal or operating pressure level 16, 18, 20. This normal operating level can be considered a normalized reference level such that pressures above this level can be considered "positive" while those below this reference level are "negative". In each case a profile of the waveform of the pressure disturbance begins with a negative going transition, 22, 24, 26, followed by a recovery portion 28, 30, 32 to an overshoot portion 34, 36, 38, producing a positive going portion, followed by a return to the reference level 16, 18, 20.

As is apparent, the duration, and therefore the period of each wave is different. As used herein, the period $Ta$, $Tb$, $Tc$ of each waveform is defined as twice the time interval from the valley 40, 42, 44 of the negative portion 22, 24, 26 of the wave to the peak 46, 48, 50 of the positive portion 34, 36, 38 of the wave. In like manner, the frequency of the wave is defined as being one divided by the period of the wave.

Waveforms corresponding to solids or semi-solids of pieces or chunks of material will generally have a period $Tb$ which is greater than that of a bubble $Ta$, while those periods $Tc$ corresponding to gun turn on/off transients are less than that of bubbles. Pressure waveforms having a period (frequency) less than (greater than) that of the range of bubbles can be filtered out as can those waveforms having periods (frequencies) greater than (less than) that of the range of bubbles by the use of, for example, a bandpass filter means. In this manner, pressure disturbances which are slow changing long duration (as compared to bubbles), such as those caused by chunks and rapidly changing short duration (as compared to bubbles) pressure disturbances, such as those caused by gun turn on/off transients can be eliminated from the signal received from the pressure transducer.

Figure 4:
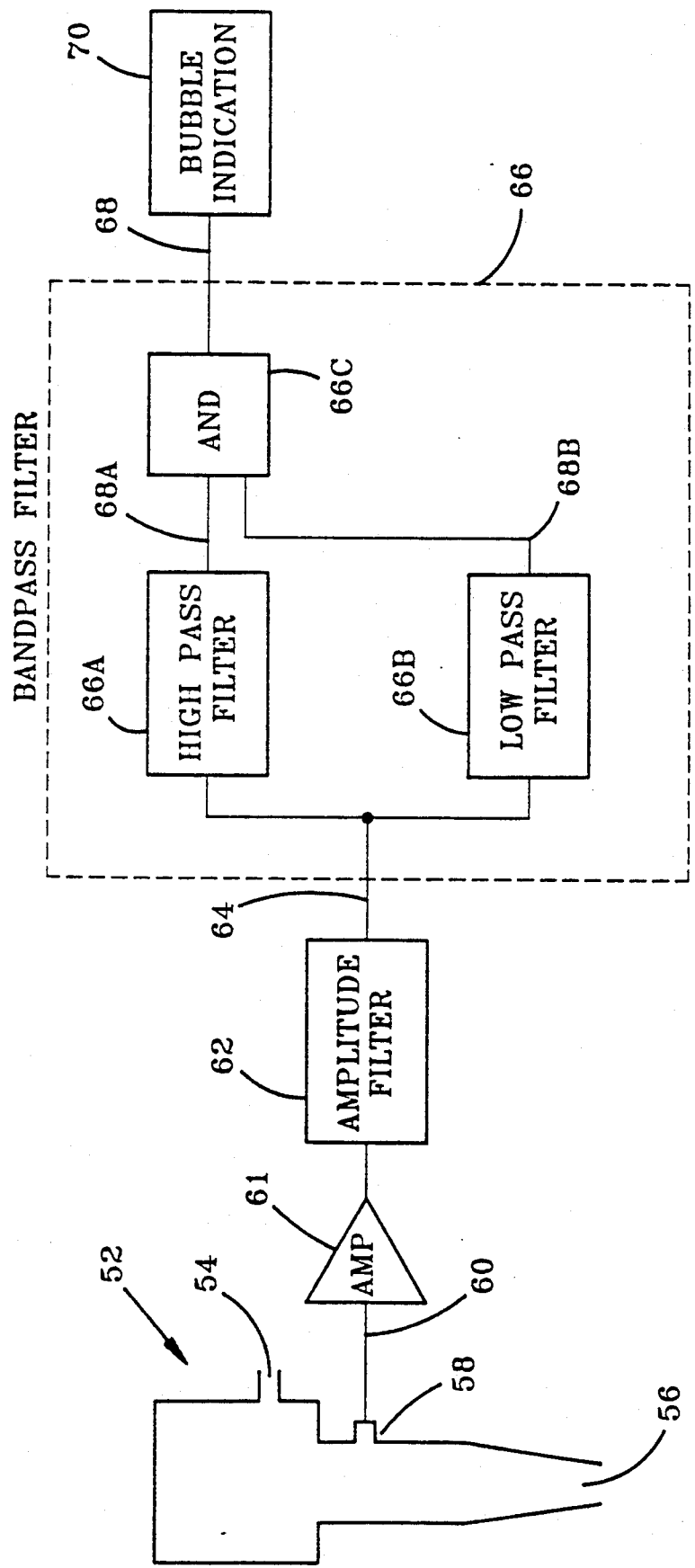
FIG. 4 is a block diagram illustrating one embodiment of the invention.

For example, with reference to FIG. 4, there is illustrated a block diagram illustrating one embodiment of the invention wherein a dispensing gun, shown generally at 52, is connected at its fluid inlet 54 with a continuous pressurized supply of fluid, for dispensing a bead of the pressurized fluid from a nozzle 56 onto a workpiece or other substrate (not shown). The nozzle 56 may be provided with a pressure sensing means 58 to continuously sense the pressure drop across the nozzle 56 and to generate a signal 60 correlated to the instantaneous pressure. The signal 60 may then be amplified by amplifier 61 and filtered through an amplitude filter 62 to eliminate those waveforms which have too small an amplitude and are therefore too small to be of interest. The filtered signal 64 then may pass to a bandpass filter means 66 for filtering out pressure transients or waveforms having periods or frequencies outside of the range of that of bubbles. The bandpass filter means 66 may comprise a high pass filter 66A and a low pass filter 66B, each receiving the signal 64. Each filter 66A, 66B generates a signal 68A, 68B if the received signal 64 passes the respective filter. The generated signals 68A, 68B are then received by an AND 66C. In response to both signals (each corresponding to a logical one) the AND 66C generates a signal 68 indicating that the signal 64 was passed by both the low and high pass filters. The signal 68 may then be received by a bubble indication means 70 which provides an indication that a bubble has occurred or passed through the nozzle 56.

The pressure sensing means 58 may comprise any suitable transducer capable of sensing the instantaneous fluid pressure, such as a strain gauge pressure transducer. One such suitable pressure transducer is manufactured by Sensotec of Columbus, Ohio. In a preferred embodiment, the dispensing gun 52 comprises a needle valve (not shown) in which the pressure transducer is located downstream of the needle valve. One particular dispensing gun suitable for use with this invention is the Pro-Flo ® dispensing gun manufactured by Nordson Corporation. While a waveform could be determined to be a bubble by comparing half the period (i.e., the time interval between the valley of the negative portion to the peak of the positive portion of the wave), a more preferred method has been found.

In determining if a waveform is in fact a bubble or not, it is preferred to compare the duration of a portion of the recovery 28, 30, 32 and the overshoot portions 34, 36, 38 to a reference. This can be accomplished by using the amplitude filter 62 to establish two different thresholds or reference levels. With reference again to FIGS. 1-3, the first reference level 72 is established as a negative reference level, while the second reference level 74 is established as a positive reference value. In each case the waveform must exceed both the first and second reference levels in order to be deemed a potential bubble. In other words, pressure disturbances levels or bubbles which do not exceed both the positive and negative reference levels are deemed to be too small to provide an adverse effect upon the bead of material.

The time intervals between reference crossings of each waveform can then be compared by the filter 66 to a reference in order to filter out rapid short duration waveforms or signals and slower changing, longer duration waveforms or signals which do not correspond to those of a bubble. For example, the time period $T1a$, $T1b$, $T1c$ between the second crossing 76, 78, 80 of the first reference level 72 to the first crossing 82, 84, 86 of the second reference level 74 can be compared to a predetermined reference $T1r$. If this time interval is greater than the reference $T1r$, then the pressure waveform is not considered to be a bubble. Those having greater transition times between reference levels crossings than the reference $T1r$ generally fall into the category of being a chunk or other solid or semi-solid material passing through the system. Therefore, the waveform of FIG. 2 would fail this test in that the time interval between transition crossings T1b would be greater than the reference T1r. However, it has been found that those waveforms having a shorter time interval between reference crossings than the reference T1r may possibly still be a bubble. Therefore, the time intervals T1a and T1c being less than the reference T1r would pass this test, and both at this time could be considered to be a potential bubble.

The next test is a measurement of the time interval between the first crossing 82, 84, 86 of the second reference level 74 and a second crossing 88, 90, 92 of the second reference level. Each time interval T2a, T2b, T2c is compared to a reference value T2r to determine if it is greater than or equal to the reference T2r. The waveform 14 of FIG. 3 has a time interval T2c which is less than the reference time interval T2r. This waveform being rapidly changing and of a short duration, such as associated with gun turn-on and turn-off, is, therefore, filtered out as a non-bubble waveform for failing the second test.

The waveform of FIG. 2, while having a time interval T2b, which is greater than the reference time interval T2r, is nevertheless filtered out as a non-bubble waveform because it did not pass the previous test. The bubble waveform 10, however, having a time interval T2a which is greater than the time interval T2r, would be considered a bubble because all tests have been passed. Therefore, an appropriate alarm or other type of indication could be activated.

Figure 5:
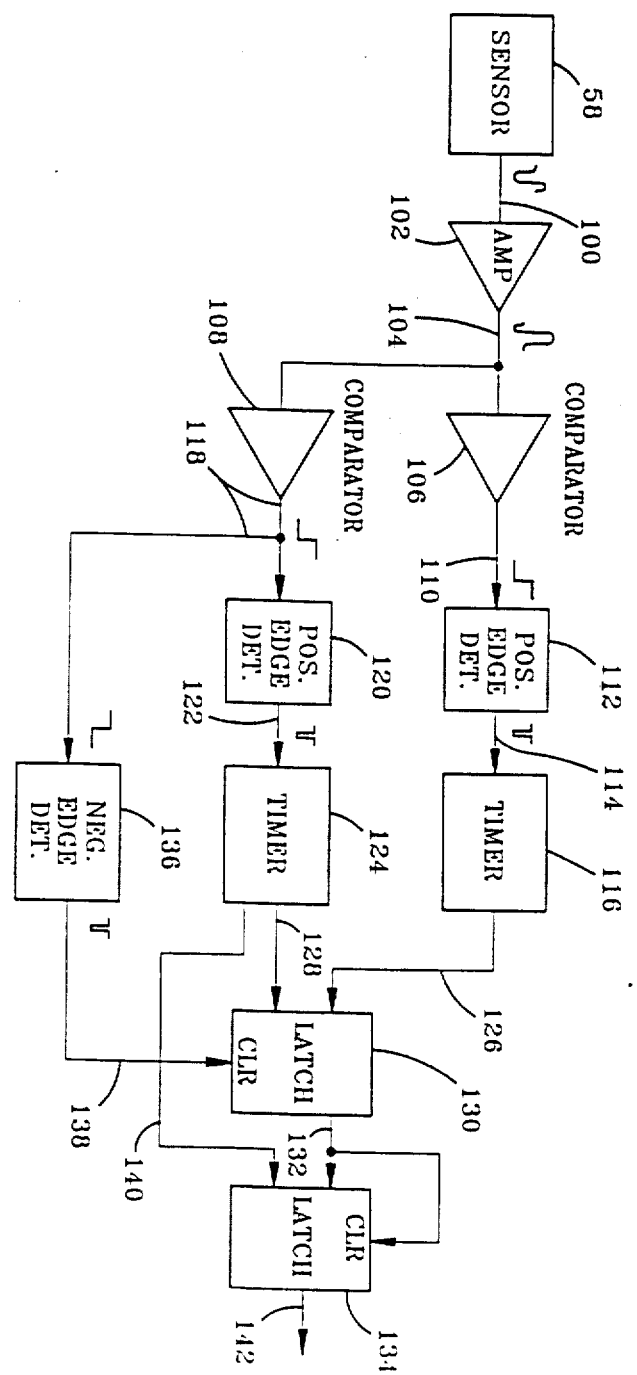
FIG. 5 is a block diagram illustrating a preferred embodiment of the invention.

Now with reference to FIG. 5, there is illustrated a block diagram for implementing a preferred embodiment of this invention. The pressure sensor means 58, such as a pressure transducer, provides an electrical signal 100 which corresponds to the continuously sensed pressure of the fluid being dispensed from the dispensing gun. This signal may be in the form of a voltage waveform which is passed through an AC amplifier 102 to remove the DC component that corresponds to the static pressure downstream of the nozzle. The amplifier 102 may be, for example, a linear amplifier or it may be a differentiating amplifier.

A linear amplifier produces an output proportional to its input. The output of a differentiating amplifier produces an output which is proportional to the rate-of-change of the input signal 60. In other words, the greater the incremental change in the input signal, the greater the output amplitude. The waveforms of FIGS. 1-3 are illustrated as being linearly amplified. However, it has been found that waveforms which have resulted due to differentiating amplification are also applicable to this method. In either case, the time intervals between crossing of the reference thresholds are compared.

Amplifier 102 amplifies, which also inverts the signal received from the pressure means 58, to produce an output signal 104 which is received by a first and second comparator 106 and 108. The first comparator 106 is configured not to conduct when the voltage is above the first reference level. The output 110 of the first comparator 106 is fed into a positive edge detection circuit 112. Therefore, when the voltage exceeds the first reference level, the output of the comparator 106 will go low and be non-conductive. When the voltage falls below the first reference level, the output of the comparator 106 will go high, corresponding to the second crossing of the first reference level. The positive edge detection circuitry 112 senses the change from the non-conductive state to the conductive state of the output of the comparator 106. When a positive edge or positive transition is sensed, the positive edge detector 112 will provide an output pulse which is fed via line 114 to a timer 116. The timer 116 upon receiving the pulse will begin timing or counting for a time interval which corresponds to the reference time interval T1r.

The second comparator 108 is conductive when the voltage of the second threshold has been exceeded and is non-conductive when the voltage of a second reference level has not been exceeded. The output 118 of the second comparator 108 is fed to a positive edge detection circuitry 120, similar to that in operation of the positive edge detection circuitry 112 above. Therefore, once the threshold of the second reference is exceeded, the output 118 will change from a low level to a high level. The positive edge detector 120 senses this transition and provides an output pulse. The output 122 of the positive edge detection circuitry 120 is fed into a second timer 124. The second timer 124 is activated upon the occurrence of the pulse from the positive edge detection circuitry 120. The time constant of timer 124 corresponds to that of the reference time interval T2r and begins timing or counting after receiving the pulse from the edge detector 120.

It should be noted that in the examples of FIGS. 1 through 3, the first reference level was a negative reference level, while the second reference level was a positive reference level. In this particular embodiment, however, because the signal has been inverted through amplification by the amplifier 102, the first reference level is now a positive reference level, while the second reference level is now a negative reference level.

The outputs 126 and 128 of timers 116 and 124 are each fed into a first latch 130. The output 126 of timer 116 will became conductive or driven high upon receiving the output 114 pulse of the positive edge detector 112, will continue to be conductive or high until the time constant T1r has been exceeded. Timer 124 begins conducting or driven high through output 128 upon the receipt of the pulse 122, and will also continue to conduct or remain high until its time interval T2r has been exceeded. The latch 130 upon the receipt of signals from both outputs 126, 128 of the timers 116, 124 will latch and produce an output signal 132 which is fed into a second latch 134. The activation of the first latch 130 corresponds to the waveform having a transition time period T1 from one reference level to the next which is less than the reference time T1r. If, however, the timer output 128 is not conductive or high until timer 116 has timed out, thereby making output 126 nonconductive or low, the first latch 130 will not latch and the waveform sensed will have failed the test as to if it is a bubble.

The output 118 from the second comparator 108 is also fed to a negative edge detection circuitry 136. The negative edge detection circuitry detects the transition from a positive or conducting state to a zero or non-conducting state. In this example this would correspond to the second crossing of the second reference level. The output 138 of the negative edge detection circuitry is fed to the clear input of the first latch 130. A second output of the timer 124 is fed via line 140 to an input of the second latch 134. The second output fed via line 140 of the timer 124 is the opposite of that of the output 128. In other words, the second output of timer 124 is non-conductive or low when the first output 128 is conductive, and is conductive or high when the first output of 128 is non-conductive. If the second timer 124 times out, which corresponds to the waveform having a transition time period T2 between crossings of the second reference level in excess of the reference time interval T2r, before the pulse is received from the negative edge detection circuitry, the second latch 134 will latch to produce an output 142 which corresponds to the detection of a bubble. If it does not, the pulse from the negative edge detector 138 will clear the first latch and, in turn, the second latch which corresponds to a disturbance which is not associated with that of a bubble.

Figure 6:
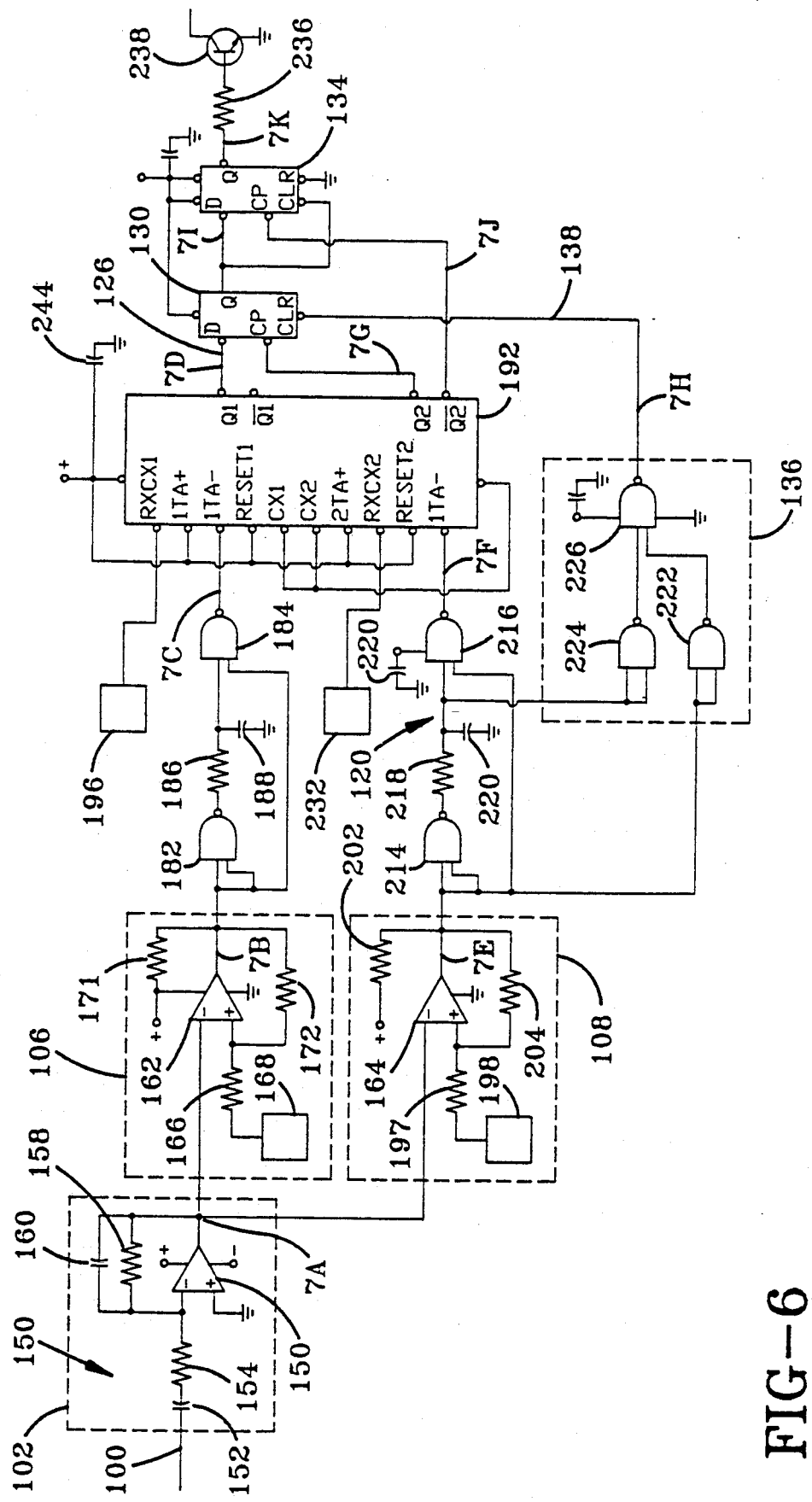
FIG. 6 is a schematic of the block diagram of FIG. 5.
Figure 7:
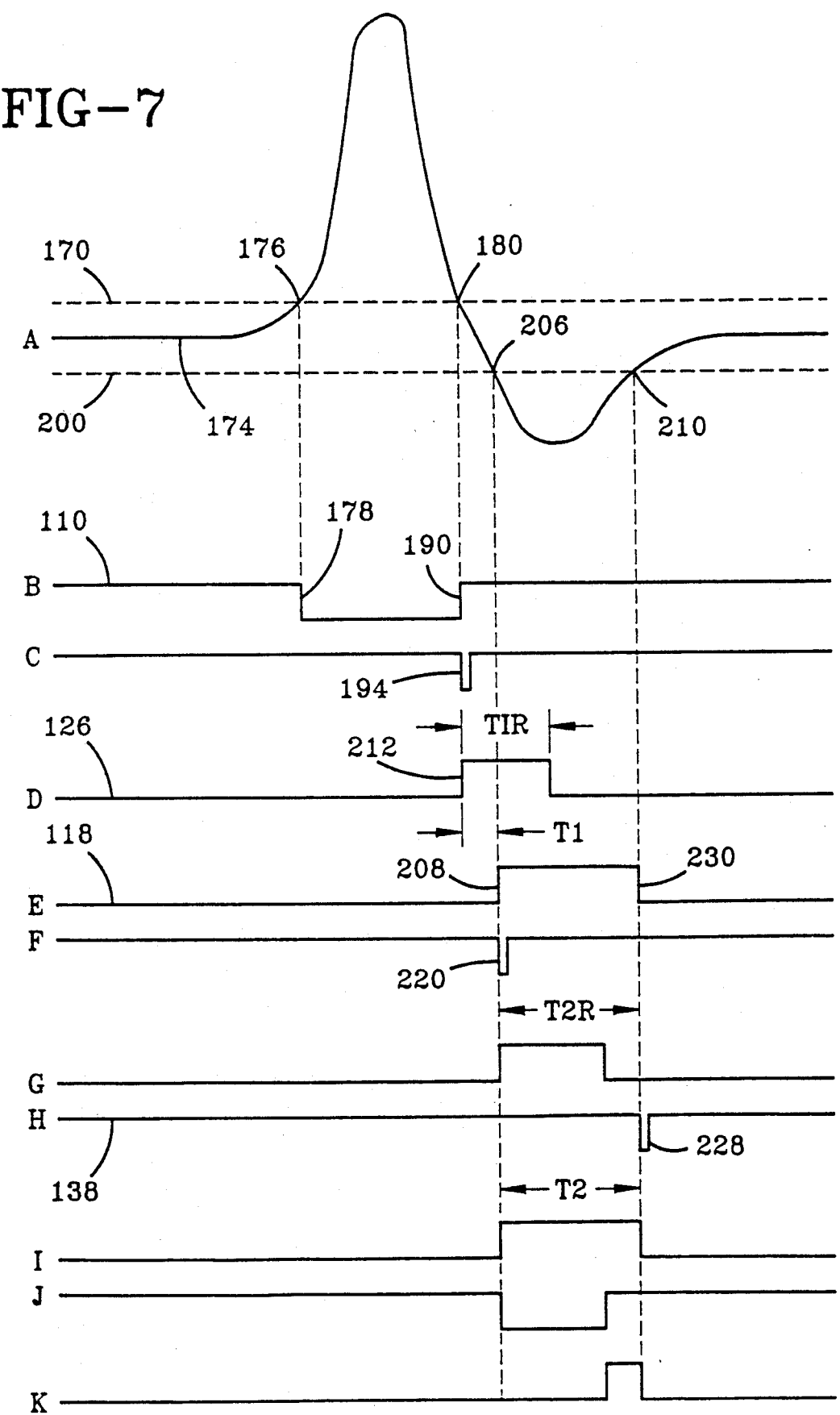
FIG. 7 shows various waveforms generated at indicated nodes of the schematic of FIG. 6.

Now, with reference to FIGS. 6 and 7, there is illustrated an electrical schematic and various associated waveforms of one embodiment of the block diagram of FIG. 5. The amplifier 102 receives the electrical signal 100 from the pressure sensor (not shown). The amplifier 102 includes a low pass filter 150 to attenuate high frequency noise. The low pass filter 150 includes a capacitor 152 and a resistor 154 connected in series between the inverting input of an operational amplifier 156 and the pressure sensor. The non-inverting input of the operational amplifier 156 is connected to ground. A feedback resistor 15 and a feedback capacitor 160 connected in parallel with one another are connected between the output of the operational amplifier 156 and its inverting input. The resulting waveform, FIG. 7A, of the output of the amplifier 102 is an amplified and inverted waveform as compared to the input waveform 100. The output of the operational amplifier 156 is connected to the inverting input of an operational amplifier 162 of the first comparator 106 and also to the inverting input of an operational amplifier 164 of the second comparator 108.

A resistor 166 is connected in series between the non-inverting input of the amplifier 162 and a referenced voltage circuit shown generally as 168. The referenced voltage circuit 168 allows the first reference level 170 to be adjustable. In other words, the magnitude of the reference level 170 may be increased or decreased depending upon a given application. This could be accomplished by a plurality of switched resistors. A resistor 171 is connected between the output of the operational amplifier 162 and the positive voltage source. A feedback resistor 172 is connected between the output of the operational amplifier 162 and its non-inverting input.

In response to the waveform of FIG. 7A, the output 110 of the first comparator 106 will be the waveform of FIG. 7B. The output of the operational amplifier 162 will be conductive or high as long as the input, waveform 174, does not exceed the first reference level 170. When the waveform 174 exceeds the first reference threshold 176, the output 110 will change state to a non-conductive or low (approximately zero) output 178, and will remain so until the waveform 174 again falls below the reference level 170 at 180. The reference circuit 168, by adjusting the first reference level 170, and thus the point at which the comparator changes state from conductive to non-conductive, allows for the adjustment of the level at which a pressure disturbance must first exceed before they are deemed a potential problem.

The output of the comparator 106 is connected to both inputs of a NAND 182, and also to one input of another NAND 184. A resistor 186 is connected in series between the output of the first NAND 182 and the other input of the second NAND 184. A capacitor 188 is connected between the resistor 186 and the input of the NAND 184 at one terminal and is grounded at the other. The resistor 186 and capacitor 188 introduces a time delay to the signal received by the NAND 184 from the first NAND 182. This time delay allows both inputs to the NAND 184 to be conductive or high when the output 110 of the comparator 106 changes from being non-conductive or low to a conductive or high state at 190. Therefore, the rising edge 190 of the waveform 110 is sensed which produces an output pulse 194 of FIG. 7C. The output of the NAND 184 is connected to the negative input (to count down) of a first counter of a timing chip 192.

Upon the receipt of the pulse 194 from the NAND 184, the output of the first counter will become conductive. The output 7D will continue to be conductive or high until the counter counts down to zero where again the output will become non-conductive or low. The length of time in which the counter will count (time) or continue to conduct after receiving the pulse 194 can be adjusted by a reference circuit 196 connected to the set point input of the first counter. This may also include a plurality of switched resistors for providing different voltage inputs to the timer. The length of time in which the counter will count in this instance is the reference time T1r. In this particular embodiment, the reference circuit 196, and, thus T1r, is adjustable from 5-50 mS. The output of the first counter is connected 126 to the input of the latch 130.

A resistor 197 is connected between a reference voltage circuit 198 and the non-inverting input of the operational amplifier 164. The reference voltage circuit 198 like that of the reference voltage circuit 168 of the first comparator 106 provides a variable input of voltage to the comparator 164. This allows for the adjustment of the second reference level 200. A resistor 202 is connected between the positive voltage source and the output of the amplifier 164. A feedback resistor 204 is connected between the output of the amplifier 164 and the non-inverting input of the amplifier 164. The output 118, FIG. 7E, of the second comparator 108 is non-conductive or low until the threshold level of the second reference 200 is exceeded 206, FIG. 7A, whereby the output becomes conductive 208 until the magnitude of the wave 174 becomes less than the reference level at 210. The time interval between when the output 126 of the first counter begins to become conductive or high to when the output 118 of the second comparator becomes conductive 208 is the time interval T1.

The output 118 of the second comparator 108 is connected to the positive edge detection circuitry 120 which is configured similarly to that of positive edge detection circuitry 112, and includes two NANDs 214, 216 and a resistor 218 and a capacitor 220. The output of the NAND 216 is connected to the negative input of a second counter of the timing chip. The output 122 of the NAND 216 produces a pulse 220, FIG. 7F, at the positive transition 208 of the waveform 118 of FIG. 7E.

Upon receipt of the pulse from the NAND 216, the output 7G of the second counter becomes conductive or low. The output of the second counter is connected to the latch input of the latch 130. The output of the first latch 130 is connected to the input and clear terminal of the second latch 134. Once the first latch 130 becomes latched, the output will become conductive.

The output of the second comparator 108 is also connected to both inputs of a NAND 222 of the negative edge detection circuitry 136. A second NAND 224 has both inputs connected between the resistor 218 and the input to the NAND 216 of the positive edge detection circuitry 120. The outputs of the NANDs 222 and 224 are connected to the inputs of a third NAND 226. The output 138 of the third NAND 226 being the output of the negative edge detection circuitry 136 is connected to the clear input of the first latch 130. The output 138 of the negative edge detection circuitry 136 produces a pulse 228 when the output 118, FIG. 7E, of the comparator 108 changes from a conductive state to a non-conductive state 230 (high to low transition).

The output 7G of the second counter when conducting represents the second reference time interval T2r. Again, the duration of T2r can be adjustable by circuitry 232 (similar to that of the reference circuit 196) connected to the reference input of the second counter. If the length of time of the second time interval T2 is less than the reference time interval T2r, then the pulse 228 produced by the negative edge detection circuitry 136 will clear the latch 130 which will reset and clear the second latch 134. The inverted output of the second counter is connected to the latching input of the second latch 134. The inverted output 7J will be positive or conductive once the counter has counted down. Therefore, when both inputs to the second latch 134 are positive, the second latch will latch producing an output 7K which may drive, for example, a resistor 236 and a power transistor 238 to provide power to an alarm circuit (not shown) for indication that a bubble has been detected.

The timing chip 192 may be a dual monostable multivibrator type CD4538, while the NANDs may be 2-input NAND gates with Schmitt-trigger inputs such as are found in the quad device type 74HC132.

Each chip should have its positive power supply pin bypassed to ground through a capacitor. Therefore, NANDS 216 and 226, and the timer chip 192 are each provided with a capacitor 240, 242, 244 to ground.

The periods of bubble waveforms may vary depending upon the material being dispensed, nozzle configuration, pressure, etc. In like manner, the settings of T1r, T2r and the threshold settings may vary depending upon these variables. However, in one particular application in which urethane was dispensed onto an automobile windshield using Nordson's Pro-Flo dispensing system, good results were obtained with T1r set at about 15 mS and T2r set at about 20 mS.

These descriptions and details have been shown for the purpose of illustrating this invention and it will become apparent to those skilled in the art that various changes and/or modifications may be made therein without departing from the original spirit or scope of the invention.

It is claimed:

1. An apparatus for detecting bubbles in pressurized liquid dispensing systems comprising:
a means for detecting pressure transients of the pressurized liquid;
a means for filtering out pressure transients having amplitudes less than predetermined reference levels
a bandpass filter means for filtering out pressure transients having a period of less than a first predetermined value and also those having a period greater than a second predetermined value, wherein non-bubble related pressure transients are filtered out, and generating a signal in response thereto; and
a bubble indication means, responsive to the signals received from the bandpass filter means, for indicating the occurrence of a bubble.

2. The apparatus of claim 1 wherein the bandpass filter means comprises comparing means, timing means, and latching means.

3. An apparatus for detecting bubbles in pressurized liquid dispensing systems comprising:
a sensor means for producing a signal in response to the pressure of the liquid;
means for comparing the signal to a first and second reference;
timing means for generating signals in response to the means for comparing; and
means, responsive to the timing means for indicating the presence of a bubble.

4. The apparatus of claim 3 further comprising an amplifier means for amplifying the signal from the sensor means; and wherein
the means for comparing the signal to a first and second reference comprising a pair of comparators; and
the timing means comprising a pair of timers.

5. The apparatus of claim 3 wherein the timing means compares time intervals between reference crossings to a respective reference.

6. The apparatus of claim 5 wherein the time intervals include a first time interval, said first time interval being the time between a second crossing of the first reference level and a first crossing of the second reference level, and a second time interval, said second time interval being the time interval between crossings of the second reference level.

7. The apparatus of claim 6 wherein the means for comparing the time intervals further comprises edge detection means and latching means.

8. The apparatus of claim 3 further comprising:
an amplifier means for amplifying the signal from the sensor means;
wherein the means for comparing comprises a first and second comparator, each receiving the amplified signal, each comparing the signal to a respective reference and generating an output signal in response thereto;
wherein the timing means comprises a first edge detection means receiving the output signal of the first comparator for producing a signal in response to changes in the output signal of the first comparator; a first timing means responsive to signals from the first edge detector means for generating a first timing signal; a second edge detection means, receiving the output signal of the first comparator for producing signals in response to changes in the output signal of the second comparator; a second timing means responsive to the second edge detection means for generating timing signals; and
wherein the means responsive to the timing means, comprises a first latch responsive to signals from the first and second timing means and the second edge detection means; a second latch responsive to signals from the first latch and the second timing means; and an alarm means responsive to signals from the second latch for indicating the presence of a bubble.

9. An apparatus for dispensing pressurized fluid material comprising:
inlet means for receiving the fluid connectable to a source of fluid;

nozzle means downstream of said inlet means for discharging the fluid;

a sensor means operably connected to said nozzle means for generating a pressure signal in response to changes in the pressure of the fluid;

an amplifier means for amplifying the generated pressure signal;

a first and second comparator, each receiving the amplified signal and comparing the amplified signal to a first and second reference level respectively; and means responsive to signals from the first and second comparators for producing a signal indicating the presence of a bubble and wherein said means includes timing means and latching means.

10. A method of detecting bubbles in pressurized liquid dispensing systems comprising the steps of:
a) dispensing the pressurized liquid from a nozzle means of a dispensing means;
b) sensing the pressure of the pressurized liquid passing through the nozzle means;
c) generating a signal in response to the pressure sensed;
d) filtering the signals by filtering out signals below a predetermined reference level, rapidly changing short duration signals and slow changing, long duration signals; and
e) indicating the occurrence of a bubble in response to the filtered signal.

11. The method of claim 10 wherein step d) comprises the steps of:
determining a first time interval, the first time interval being the time between a second crossing of a first reference level and a first crossing of a second reference level by the signal; and
comparing said first time interval to a first reference time interval.

12. The method of claim 11 wherein step d) comprises the steps of:
determining a second time interval, the second time interval being the time between the first and a second crossing of the second reference level by the signal; and
comparing said second time interval to a second reference time interval.

13. The method of claim 12 wherein the first and second reference levels are diametrically opposed to one another about a normal operating reference level.

14. A method of detecting bubbles in a pressurized liquid dispensing system comprising the steps of:
detecting the pressure of the pressurized liquid passing through a dispensing means and generating a signal in response thereto;
detecting the leading edge of a transient waveform of said generated signal;
detecting a recovery portion of waveform and determining the rate of change of a portion of the recovery portion of the waveform; and
detecting an overshoot portion of the waveform and determining a rate of change of a portion of the overshoot portion.

15. The method according to claim 14 further comprising the step of first amplifying the generated signal.

16. The method of claim 15 wherein the signal is linearly amplified.

17. The method of claim 15 wherein the signal is differentially amplified.

18. A method of detecting bubbles in a pressurized liquid dispensing system comprising the steps of:
a) detecting the instantaneous pressure of the pressurized liquid passing through a dispensing means and generating a signal in response thereto;
b) amplifying the signals;
c) detecting a recovery portion of a waveform generated by said amplified signals and determining over a predetermined interval of the recovery portion a first time interval;
d) detecting an overshoot portion of the waveform and determining over a predetermined interval of the overshoot portion a second time interval;
e) comparing the first and second time intervals to a first and second reference respectively, and indicating the presence or absence of a bubble in response to said comparing.

19. The method of claim 18 where the step of comparing comprises the following steps:
aa) determining if the first time interval is less than the first reference;
bb) determining if the second time interval is greater than the second reference; and
cc) indicating the occurrence of a bubble if both steps (aa) and (bb) are true.

* * * * *

UNITED STATES PATENT AND TRADEMARK OFFICE
CERTIFICATE OF CORRECTION

PATENT NO. : 5,182,938

Page 1 of 2

DATED : February 2, 1993

INVENTOR(S) : Stephen L. Merkel

It is certified that error appears in the above-identified patent and that said Letters Patent is hereby corrected as shown below:

In the Drawings:

Figure 5, should be added as shown on the attached sheet.

Signed and Sealed this

Seventh Day of June, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,182,938
DATED : February 2, 1993
INVENTOR(S) : Stephen L. Merkel

It is certified that error appears in the above-identified patent and that said Letters Patent is hereby corrected as shown below:

On Col. 7, line 24, delete "15" and insert in place thereof --158--.

On Col. 12, line 11, insert --the-- between "of" and "waveform".

Signed and Sealed this

Fourteenth Day of February, 1995

Attest:

BRUCE LEHMAN

*Attesting Officer*  *Commissioner of Patents and Trademarks*